(12) United States Patent
Klockow et al.

(10) Patent No.: US 9,351,837 B2
(45) Date of Patent: May 31, 2016

(54) SOCKET, IN PARTICULAR AN ACETABULAR SOCKET FOR A HIP ENDOPROSTHESIS

(75) Inventors: Andreas Klockow, Liestal (CH); Pius Odermatt, Buochs (CH)

(73) Assignee: Smith & Nephew Orthopaedics AG, Rotkreuz (CH)

( * ) Notice: Subject to any disclaimer, the term of this patent is extended or adjusted under 35 U.S.C. 154(b) by 56 days.

(21) Appl. No.: 13/978,314

(22) PCT Filed: Jan. 12, 2011

(86) PCT No.: PCT/EP2011/050336
§ 371 (c)(1),
(2), (4) Date: Jul. 3, 2013

(87) PCT Pub. No.: WO2012/095168
PCT Pub. Date: Jul. 19, 2012

(65) Prior Publication Data
US 2013/0289736 A1    Oct. 31, 2013

(51) Int. Cl.
*A61F 2/34* (2006.01)
*A61F 2/30* (2006.01)

(52) U.S. Cl.
CPC ........... *A61F 2/34* (2013.01); *A61F 2002/3053* (2013.01); *A61F 2002/30378* (2013.01); *A61F 2002/30505* (2013.01); *A61F 2002/30532* (2013.01); *A61F 2002/3403* (2013.01); *A61F 2002/3424* (2013.01); *A61F 2002/3438* (2013.01); *A61F 2220/0025* (2013.01)

(58) Field of Classification Search
CPC ................. A61F 2002/3409; A61F 2002/3411
USPC ........... 623/22.21–22.24, 22.28, 22.32, 22.37
See application file for complete search history.

(56) References Cited

U.S. PATENT DOCUMENTS 5,725,519 A * 3/1998 Penner et al. ..................... 606/1
5,725,591 A * 3/1998 DeCarlo et al. ............ 623/22.29

FOREIGN PATENT DOCUMENTS

DE          29516473 U1 * 10/1995 .......... A61F 2/30744

* cited by examiner

*Primary Examiner* — Yashita Sharma
*Assistant Examiner* — Daniel Bissing
(74) *Attorney, Agent, or Firm* — Taft Stettinius & Hollister LLP

(57) ABSTRACT

An acetabular socket (1) for a hip endoprosthesis comprises a socket shell (7) and a socket insert (8). The socket shell (7) is configured for implantation in a pelvic bone (2) of a patient and has an inner surface (12) that defines an accommodating space (10) extending about an axis of rotation (11). The socket insert (8) is coupleable with the socket shell (7) and is configured to provide a bearing for a joint head (6) of a prosthesis stem (3). The socket insert (8) has an outer surface (14) configured to be seated in the accommodating space (10) of the socket shell (7). A moveable anti-lock means (17) is provided between the socket shell (7) and the socket insert (8). In a first position the anti-lock means (17) restrains the socket insert (8) from seating within die accommodating space (10) of the socket shell (7) but the anti-lock means (17) is moveable into a second position wherein the socket insert (7) is capable of seating within the socket shell (7) and of coupling therewith. The anti-lock means (17) preventing the socket insert (8) from prematurely locking into an undesirable position in the socket shell (7) prior to correct positioning and orientation by a surgeon during implantation.

8 Claims, 5 Drawing Sheets

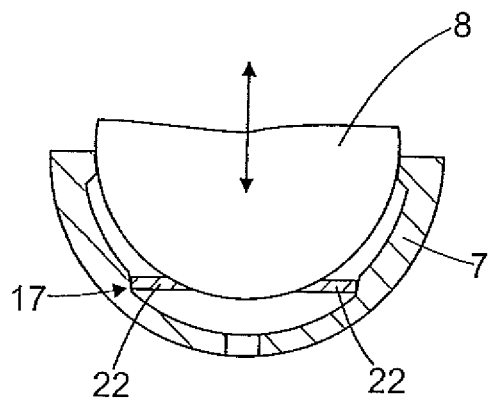 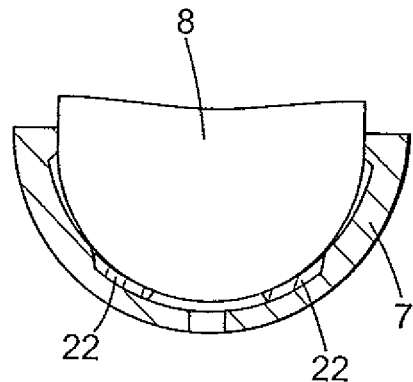
Fig. 5a    Fig. 5b
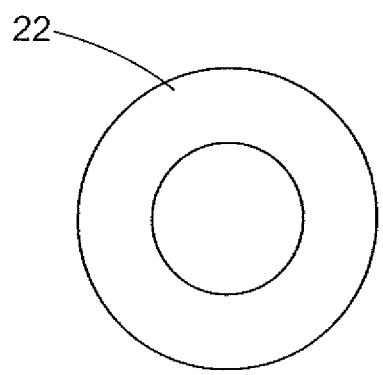 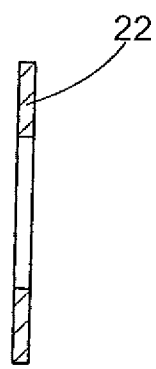
Fig. 6a    Fig. 6b

SOCKET, IN PARTICULAR AN ACETABULAR SOCKET FOR A HIP ENDOPROSTHESIS

This application is a United States National Phase filing of International Application No. PCT/EP11/050336 filed on Jan. 12, 2011, which is incorporated herein by reference.

The present invention relates to a socket, in particular an acetabular socket for a hip endoprosthesis.

In the case of total hip endoprosthesis, a prosthesis stem having a joint head is inserted into the femur. An acetabular socket, which serves as a bearing shell for the joint head, is implanted in the pelvic bone. It is known to construct the acetabular socket from a socket shell and a socket insert. In this way the socket shell can be optimized with regard to implantation in the pelvic bone and the socket insert can be optimized with regard to the bearing properties for the joint head. In these cases the socket shell is formed and positioned in the pelvic bone so that it is as stable as possible. The socket insert is then oriented in the socket shell in such a way that the joint head is accommodated so that the prosthesis stem and accordingly the femur of the patient are as far as possible in the correct orthopaedic position. The aforementioned situation does also apply to sockets of other kinds of endoprothesis, such as shoulder endoprothesis or the like.

In EP 0 663 193 A1 is disclosed an acetabular socket wherein the socket insert has a spherical outer surface and is seated in a corresponding spherical accommodating space with the same spherical radius in the socket shell. Therefore, when the socket insert has been inserted into the socket shell, the socket insert can be rotated at will about its axis of rotation and its axis of rotation can be tilted at will with respect to the axis of rotation of the accommodating space. As a result, it is possible for the socket shell to be positioned in the pelvic bone in accordance with the bone structure and for the socket insert to be oriented in accordance with the orthopaedic position of the prosthesis stem inserted into the femur. In order to fix the socket insert in its position within the socket shell, the inner spherical surface of the accommodating space of the socket shell has pointed projecting teeth which engage in the outer surface of the socket insert. Because the teeth have to dig into the outer surface of the socket insert, there are limitations with respect to the choice of material for the socket insert. Pressing the socket insert onto the teeth of the socket shell makes it difficult for the socket insert to be inserted in a precisely positioned manner.

This problem was overcome as described in WO2005/063148. Here an acetabular socket for a hip endoprosthesis consists of a socket shell and a socket insert wherein the socket shell has an accommodating space having a conical inner surface in which the spherical outer surface of the socket insert is inserted. Because fixing of the optimally oriented socket insert results from its being simply pressed into the accommodating space, this fixing is simple to carry out and does not require any additional instrumentation or additional fixing means. As a result, the socket insert can be clamped in self-retaining manner in any desired position of rotation and tilt in the accommodating space of the socket shell.

In order to bring about reliable clamping of the socket insert in the socket shell, the socket insert and the socket shell are made from a hard material. The socket shell is preferably manufactured from a biocompatible material, for example a titanium alloy. For the socket insert there can be selected a material corresponding to the sliding characteristics pairing of socket shell and joint head, for example a metallic or ceramic material or a plastics material.

However, it has been found that when a socket insert is first inserted into a socket shell it tends to lock in position. This may be caused the conical/spherical interface between the two components. The surgeon is then required to use surgical instruments to free the socket insert so that it can be orientated correctly in a precisely positioned manner before being pressed into the desired position in the socket shell.

It is an object of the present invention to provide a socket, in particular an acetabular socket for a hip endoprosthesis that overcomes the aforementioned problem by preventing a socket insert from locking into an undesirable position in a socket shell prior to correct positioning and orientation.

According to the present invention there is provided a socket, in particular an acetabular socket for a hip endoprosthesis comprising
  a socket shell configured for implantation in a pelvic bone of a patient and having an inner surface that defines an accommodating space and
  a socket insert coupleable with the socket insert and configured to provide a bearing for a joint head of a prosthesis stem and having an outer surface configured to be seated in the accommodating space of the socket shell;
  characterised in that a moveable anti-lock means is provided between the socket shell and the socket insert which in a first position restrains the socket insert from seating within the accommodating space of the socket shell and which is moveable into a second position wherein the socket insert is capable of seating within the socket shell and of coupling therewith.

The provision of an anti-lock means as aforesaid prevents a premature locking of the socket insert in the socket shell. This allows the socket shell to be implanted in a pelvic bone in accordance with the bone anatomy and structure of the pelvic bone so that optimum conditions for ingrowth can be achieved. The socket insert can then be freely oriented in relation to the socket shell in an uncoupled position during surgery to enable a surgeon to follow a standard protocol in adjusting the relative position of the socket insert to the socket shell. In particular the socket insert can be rotated in the socket shell and its axis of rotation can be so tilted in relation to the axis of rotation of the socket shell so that the axis of rotation of the socket insert is aligned with the axis of the shaft neck of the prosthesis stem when the femur with the inserted prosthesis stem is arranged in the optimum orthopaedic position. In addition, the invention allows reduction and a range of motion testing by the surgeon while the socket insert is uncoupled from the socket shell. Only when the surgeon is satisfied that the optimum relative position of the socket insert to the socket shell has been achieved will the anti-lock means be moved to enable the socket insert to be coupled to the socket shell.

In embodiments such as those described below wherein the socket insert is coupleable to the socket shell in a self-locking manner within said accommodating space, then the anti-lock means is moved by the application of pressure to the socket insert in a direction pushing it into accommodating space. This action simultaneously moves the anti-lock means into its second position allowing the socket insert to become clamped in the accommodating space in self-retaining manner. However, it should be appreciated that the invention is also suitable for use with socket inserts and socket shells that have a spherical/spherical interface and will again prevent premature locking of the two components together.

Embodiments of the present invention will now be described by way of example with reference to the accompanying drawings, in which FIG. 1 is a diagram showing schematically a total hip endoprosthesis using an acetabular socket in accordance with a first embodiment of the present invention;

FIGS. 5a and 5b are diagrams similar to FIG. 2 but of a second embodiment of acetabular socket in accordance with the invention when respectively in an uncoupled state and in a coupled state;

FIGS. 6a and 6b are plan and side views of an annulus forming part of the second embodiment of acetabular socket shown in FIGS. 5a and 5b;

Figure 1:
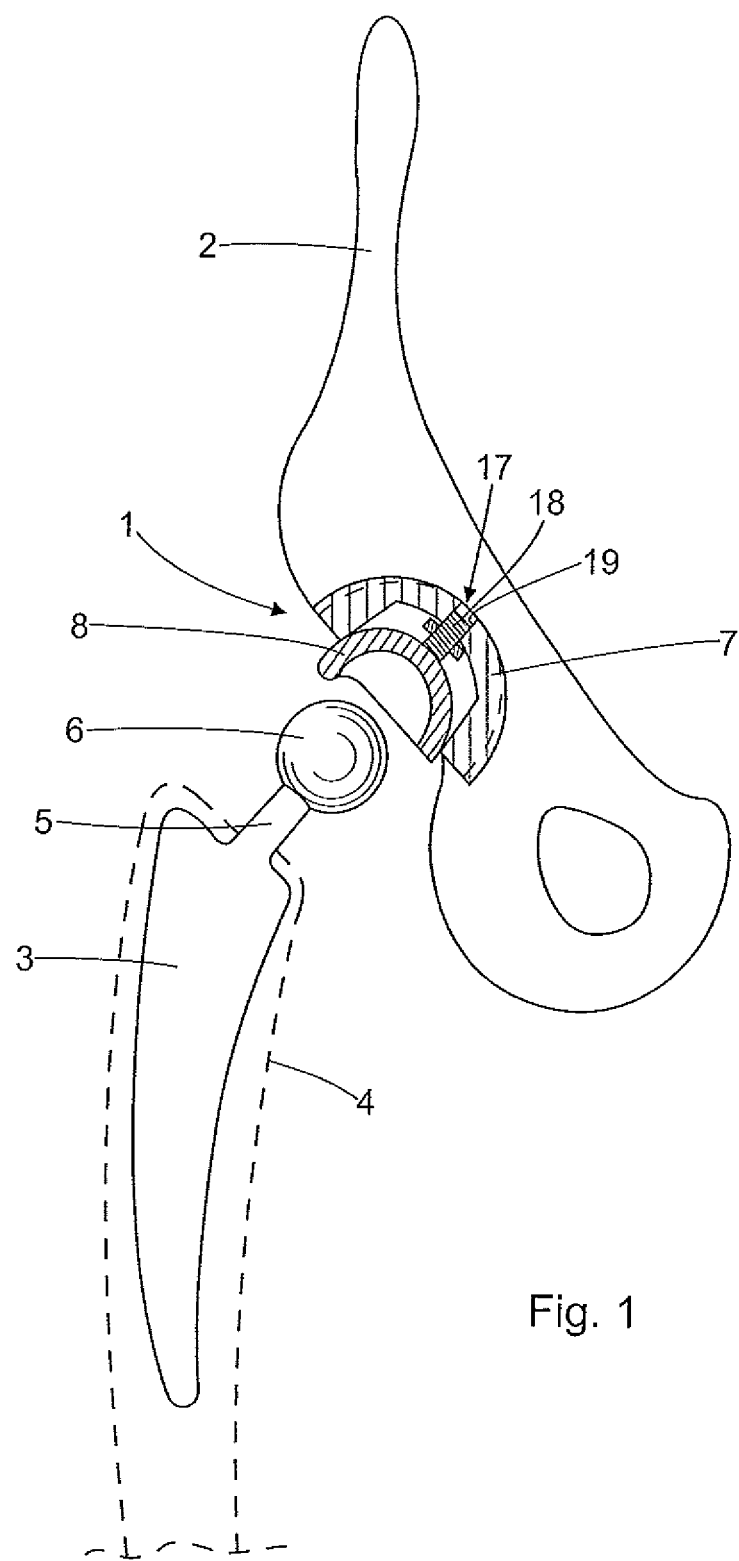

A total hip endoprosthesis comprises an acetabular socket 1 for implantation in the pelvic bone 2 of a patient and a prosthesis stem 3 for implantation into the femur 4. The prosthesis stem 3 has a shaft neck 5 that carries a joint head 6 which is inserted into the acetabular socket 1. The acetabular socket 1 comprises a socket shell 7 and a socket insert 8. The socket shell 7 is adapted to be inserted in the pelvic bone 2 in a conventional manner, for example by being pressed in with appropriate gripping structures 9 on its outer surface, by screwing or by the use of appropriate fasteners (not shown). The socket shell 7 is substantially hemispherical and is recessed to provide an accommodating space 10 that is open to the equatorial plane and that at least in the region in which it comes into contact with the outer surface of the socket insert has rotational symmetry with respect to the mid-axis 11 of the socket shell 7.

In all of the illustrated embodiments of the present invention, the accommodating space 10 has an inner surface 12 in the form of a straight circular cone which becomes narrower from the opening located in the equatorial plane towards the pole of the socket shell 7. A base 13 of the accommodating space 10 is flattened off in the pole region. The angle between the conical inner surface 12 and the axis of rotation 11 is selected dependent on the material pairing of the socket shell 7 and the socket insert 8 so that self-retention will come about when the socket insert 8 is pushed into the socket shell 7. This angle is preferably between 4° and 10°.

The socket insert 8 also has a substantially hemispherical shape. Its outer surface 14 is spherically shaped, at least in the region in which it comes into contact with the inner surface 12 of the accommodating space 10. It also has a recessed spherical bearing surface 15, which serves to accommodate, and provide a bearing for, the joint head 6. The spherical outer surface 14 and the spherical bearing surface 15 at least in the region of contact are rotationally symmetrical with respect to an axis of rotation 16 of the socket insert 8.

In order to restrain the socket insert 8 from prematurely seating within the accommodating space 10 of the socket shell 7 during surgery, a moveable anti-lock means 17 is provided between the socket shell 7 and the socket insert 8. This means 17 holds the socket insert 8 in an elevated position relative to the socket shell 7 until the surgeon is ready couple the socket insert 8 to the socket shell 7.

Figure 2:
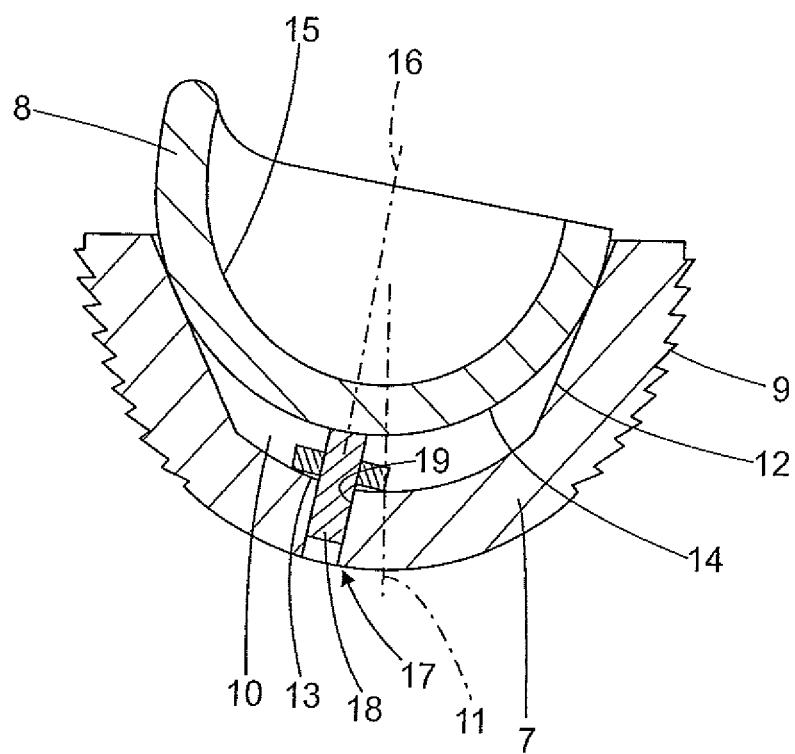
FIG. 2 is an axial section through the acetabular socket shown in FIG. 1 but to an enlarged scale, the acetabular socket being shown in an uncoupled position.
Figure 3A:
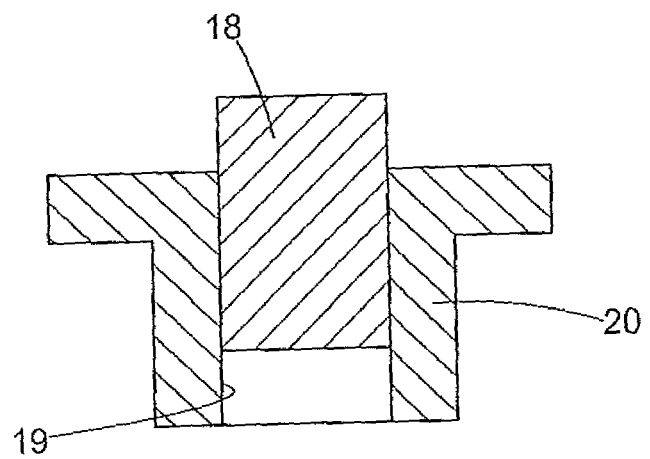
FIGS. 3a and 3b are scrap diagrammatic views showing an anti-lock means forming part of the acetabular socket shown in FIG. 2 respectively in an anti-lock position and in a position adopted after locking of the acetabular socket.
Figure 3B:
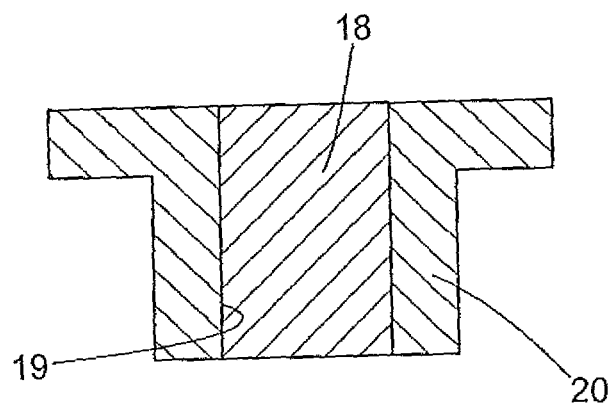

In the first embodiment shown in FIG. 2, the anti-lock means 17 comprises a pin 18 which is push-fitted within a central channel 19 of a screw fitting 20 or similar located at the pole of the socket shell 7. The length of the pin 18 is commensurate with the length of the channel 19 so that it can be accommodated at least partly, and preferably completely within the channel 19, as shown in FIG. 3b. However, initially, it is left projecting out of the channel 19 as shown in FIG. 3a. The projecting end of the pin 18 therefore prevents the socket insert 8 from seating within the socket shell 7, as shown in FIG. 2. However, when the socket insert 8 has been optimally oriented and it is desired to couple the socket insert 8 to the socket shell 7, pressing of the socket insert 8 axially into the accommodating space 10 will also push the pin 18 into the channel 19 so that it no longer projects this enables the insert 8 to be coupled to the shell 7 in a self-retaining manner in that orientation position.

Figure 4:
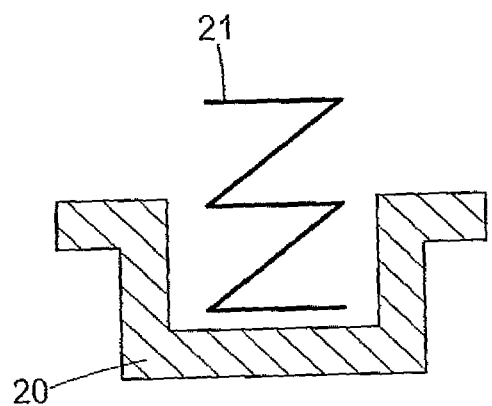
FIG. 4 is a scrap diagrammatic view showing a modified arrangement of an anti-lock means forming part of the acetabular socket.

It will be appreciated that the pin 18 and channel 19 arrangement may be modified and still perform the same function. For example, as shown in FIG. 4, the pin 18 may be replaced by a spring 21 or an equivalent elastic means, for example a rubber or plastics plug or similar, that is compressed into the channel 19 when the socket insert 8 is pressed into the socket shell 7. Alternatively, the pin 18 may be made freely movable within the channel 19 but retained in a projecting position by a spring or an equivalent elastic means not shown) located beneath it in the channel 19. In these cases, the strength of the spring or elastic means needs to be sufficient to support the socket insert 8 but not so strong that it significantly impedes coupling of the socket insert 8 in the socket shell 7 when the former is pushed into place.

In addition, it will be appreciated that it may also be possible for the pin 18, spring or elastic member to project from a channel defined in the outer surface 14 of the socket insert 8 and to be pushed into this channel when the socket insert 8 is pushed into the socket shell 7 to couple therewith.

Preferably but not necessarily, the pin 18, spring or elastic member is aligned with the mid-axis 11 at the pole of the socket shell 7. This position is that which tends to receive the greatest force when the socket insert 8 is pressed into the socket shell 7.

A second embodiment of the invention is shown in FIGS. 5a and 5b. Here the anti-lock means 17 comprises a thin, flexible annular disc 22, as shown in FIGS. 6a and 6b, that is located within the socket shell 7 beneath the socket insert 8. Such a disc 22 may comprise a disc spring, a springy, flexible washer or similar means that is capable of being flexed out of a planar position. Initially, the disc 22 is planar and therefore holds the socket insert 8 in an elevated position relative to the socket shell 7, as shown in FIG. 5a, thereby preventing premature locking of the insert 7 in the shell 7. However, when it is desired to couple and thereby to lock the socket insert 8 into the socket shell 7, pressing of the socket insert 8 axially into the accommodating space 10 will cause the disc 22 to flex so that it is clamped between the inner surface 12 of the accommodating space 10 and the outer surface 14 of the socket insert 8. Again, the strength of the springiness of the disc 22 should only be sufficient to support the socket insert 8 but not so strong that it impedes coupling of the socket insert 8 in the socket shell 7.

In a modification, the anti-lock means 17 may comprise a compressible ring rather than an annular disc 22 so that rather than flexing into a second position when the socket insert 8 is pressed into the socket shell 7, it is compressed between the inner surface 12 of the accommodating space 10 and the outer surface 14 of the socket insert 8.

In a further modification the anti-lock means 17 may comprise a compressible spring leaf, pin, membrane or the like rather than an annular means, which may be deformed in a similar way as described above when the insert 8 is pressed into the socket shell 7.

In addition, the disc 22 or ring may be arranged to form part of or be secured to the outer surface 14 of the socket insert, for example by projecting from an annular groove formed in the outer surface 14, rather than comprising an separate component or a component secured in a similar way to the inner surface 12.

Figure 7:
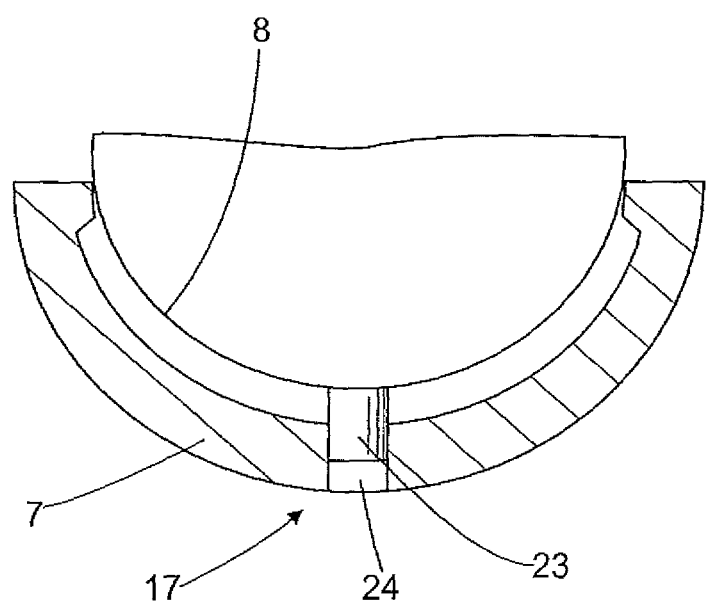
FIG. 7 is a diagram similar to FIG. 2 but of a third embodiment of acetabular socket in accordance with the invention.

A third embodiment of the invention is shown in FIG. 7. In this acetabular socket, a pin 23 is used to predefine the angulation of the socket insert 8 to the socket shell 7 in addition to providing the anti-lock means 17. In the illustrated arrangement shown in FIG. 7, the pin 23 is fixed, moulded or otherwise secured to the outer surface 14 of the socket insert 8 in a predetermined position which in this case is at its pole although other predetermined positions are possible. The pin 23 is designed to be a push fit in a channel 24 formed in the base 13 of the accommodating space 10, again at a predetermined position which in this case is at the pole. In use, the pin 23 prevents the socket insert 8 from being prematurely locked into the socket shell 7. However, it also requires the socket insert 8 to be angulated correctly with the socket shell 7 before coupling can take place as for this to occur the pin 23 must be pushed into the channel 24.

It will be appreciated that modifications to the aforementioned arrangement are possible. For example, the pin 23 could be secured to the socket shell 7 and penetrate a channel or cavity formed in the outer surface 14 of the socket insert 8. The pin 23 could also be arranged to project out of a cavity defined in either the socket shell 7 or the socket insert 8 and to penetrate a corresponding channels or cavity in the other component so as to form a bridge between them. It will also be appreciated that the pin 23 could be spring-loaded or otherwise biased and retained in a projecting position by a spring or an equivalent elastic means (not shown) located beneath it in a channel. In such an arrangement the pin 23 will click into position within the channel or cavity in the other component.

In other arrangements, a plurality of channels may be provided in the shell 7 or the insert 8 and the surgeon left to decide which one of these a pin secured to the other part of the acetabular socket is to be pushed during coupling of the two components 7, 8. In yet a further modification, this pin arrangement may be combined with the second embodiment described above so that effectively the acetabular socket comprises two separate anti-lock means.

In all of the illustrated embodiments, the accommodating space 10 has an inner surface 12 in the form of a straight circular cone as described above. However, it will be appreciated that it is also possible to make use of the invention in acetabular sockets wherein the accommodating space is hemi-spherical as described in EP 0 663 193 A1 or has another profile as in all cases the invention can be used to prevent a locking of the socket insert 8 in the socket shell 7 prior to the correct positioning of the socket insert 8 within the socket shell 7.

It may be mentioned that the anti-locking means 17, e.g. in form of the pin 18 can be aligned with a pole of the socket shell 7, or alternatively with a pole of the insert 8 in case that the anti-locking means 17 is associated to the insert 8 instead of the socket shell 7. It may be preferred that the aforementioned locking-means 17 are placed eccentrically in relation to the axis of rotation of either the socket shell or insert respectively. The angle of eccentricity is up to 25°, preferably between 5° to 15°.

Further, it may be mentioned that the present invention applies to sockets for all kinds of joints, such as hip joints, shoulder joints, or the like, each comprising a socket shell and a socket insert.

REFERENCE NUMERALS

1 Acetabular socket
2 Pelvic bone
3 Prosthesis stem
4 Femur
5 Shaft neck
6 Joint head
7 Socket shell
8 Socket insert
9 Gripping structures
10 Accommodating space
11 Mid-axis of socket shell
12 Inner surface of socket shell
13 Base of accommodating space
14 Outer surface of socket insert
15 Spherical bearing surface
16 Axis of rotation of socket insert
17 Anti-lock means
18 Pin
19 Channel
20 Screw fitting
21 Spring
22 Annular disc
23 Pin
24 Channel

What is claimed is:

1. An acetabular socket for a hip endoprosthesis, comprising:
   a socket shell configured for implantation in a pelvic bone of a patient and having an inner surface that defines an accommodating space; and
   a socket insert coupleable with the socket shell and configured to provide a bearing for a joint head of a prosthesis stem and having an outer surface configured to be seated in the accommodating space of the socket shell;
   wherein a moveable anti-lock means is provided between the socket shell and the socket insert which in a first position restrains the socket insert from seating within the accommodating space of the socket shell and which is moveable into a second position wherein the socket insert is capable of seating within the socket shell and of coupling therewith;
   wherein the anti-lock means comprises a pin which in the first position is at least partially located between the inner surface of the socket shell and the outer surface of the socket insert, and which in the second position is located in a channel defined in at least one of the socket shell and the socket insert; and
   wherein the pin is push-fit within the channel.

2. An acetabular socket as claimed in claim 1, wherein coupling of the socket insert with the socket shell by pushing the socket insert into the socket shell moves the anti-lock means from its first position into its second position.

3. An acetabular socket as claimed in claim 1, wherein the pin predefines the angulation of the socket insert to the socket shell.

4. An acetabular socket as claimed in claim 1, wherein in its first position the pin projects from the channel and in its second position is accommodated at least partially within the channel.

5. An acetabular socket for a hip endoprosthesis, comprising:
a socket shell configured for implantation in a pelvic bone of a patient and having an inner surface that defines an accommodating space; and
a socket insert coupleable with the socket shell and configured to provide a bearing for a joint head of a prosthesis stem and having an outer surface configured to be seated in the accommodating space of the socket shell;
wherein a moveable anti-lock means is provided between the socket shell and the socket insert which in a first position restrains the socket insert from seating within the accommodating space of the socket shell and which is moveable into a second position wherein the socket insert is capable of seating within the socket shell and of coupling therewith;
wherein the anti-lock means comprises a pin which in the first position is at least partially located between the inner surface of the socket shell and the outer surface of the socket insert, and which in the second position is located in a channel defined in at least one of the socket shell and the socket insert; and
wherein the pin is retained in the first position by a spring or an elastic means located beneath it in the channel.

6. An acetabular socket as claimed in claim 5, wherein the spring or elastic means is compressed within the channel when the pin is in the second position.

7. An acetabular socket as claimed in claim 5, wherein the pin is aligned with a pole of the socket shell or the pole of the insert.

8. An acetabular socket as claimed in claim 5, wherein the accommodating space has an inner surface in the form of a straight circular cone which becomes narrower from in a direction towards a pole of the socket shell whereby the socket insert is seated within and thereby coupled with the socket shell in a self-locking manner by being pressed into the accommodating space.

* * * * *